US011324749B2

(12) United States Patent
Assad

(10) Patent No.: US 11,324,749 B2
(45) Date of Patent: May 10, 2022

(54) COMBINATION THERAPY FOR TREATMENT OF HEMATOLOGICAL DISEASES

(71) Applicant: Incyte Corporation, Wilmington, DE (US)

(72) Inventor: Albert Assad, Jersey City, NJ (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 16/670,289

(22) Filed: Oct. 31, 2019

(65) Prior Publication Data

US 2020/0129517 A1 Apr. 30, 2020

Related U.S. Application Data

(60) Provisional application No. 62/753,409, filed on Oct. 31, 2018.

(51) Int. Cl.
| | | |
|---|---|---|
| *A61K 31/519* | (2006.01) | |
| *A61P 35/00* | (2006.01) | |
| *A61K 31/4015* | (2006.01) | |
| *A61K 31/454* | (2006.01) | |
| *A61K 31/573* | (2006.01) | |

(52) U.S. Cl.
CPC ........ *A61K 31/519* (2013.01); *A61K 31/4015* (2013.01); *A61K 31/454* (2013.01); *A61K 31/573* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 7,335,667 | B2 | 2/2008 | Rodgers et al. |
| 7,598,257 | B2 | 10/2009 | Rodgers et al. |
| 7,834,022 | B2 | 11/2010 | Rodgers et al. |
| 8,158,616 | B2 | 5/2012 | Rodgers et al. |
| 8,309,718 | B2 | 11/2012 | Li et al. |
| 8,410,265 | B2 | 4/2013 | Zhou et al. |
| 8,486,902 | B2 | 7/2013 | Rodgers et al. |
| 8,513,270 | B2 | 8/2013 | Arvanitis et al. |
| 8,563,541 | B2 | 10/2013 | Arvanitis et al. |
| 8,604,043 | B2 | 12/2013 | Li et al. |
| 8,691,807 | B2 | 4/2014 | Yao et al. |
| 8,716,303 | B2 | 5/2014 | Rodgers et al. |
| 8,722,693 | B2 | 5/2014 | Rodgers et al. |
| 8,765,734 | B2 | 7/2014 | Huang et al. |
| 8,933,085 | B2 | 1/2015 | Rodgers et al. |
| 8,987,443 | B2 | 3/2015 | Liu et al. |
| 9,034,884 | B2 | 5/2015 | Rodgers et al. |
| 9,181,271 | B2 | 11/2015 | Li et al. |
| 9,193,733 | B2 | 11/2015 | Rodgers et al. |
| 9,249,145 | B2 | 2/2016 | Rodgers et al. |
| 9,358,229 | B2 | 6/2016 | Vannucchi et al. |
| 9,359,358 | B2 | 6/2016 | Rodgers et al. |
| 9,382,231 | B2 | 7/2016 | Li et al. |
| 9,487,521 | B2 | 11/2016 | Zhou et al. |
| 9,498,467 | B2 | 11/2016 | Leopold |
| 9,655,854 | B2 | 5/2017 | Yeleswaram et al. |
| 9,802,957 | B2 | 10/2017 | Zhou et al. |
| 9,993,480 | B2 | 6/2018 | Vannucchi et al. |
| 10,166,191 | B2 | 1/2019 | Ni et al. |
| 10,596,161 | B2 | 3/2020 | Koblish et al. |
| 10,899,736 | B2 | 1/2021 | Wang et al. |
| 2006/0106020 | A1 | 5/2006 | Rodgers et al. |
| 2010/0113416 | A1 | 5/2010 | Friedman et al. |
| 2010/0298334 | A1 | 11/2010 | Rodgers et al. |
| 2011/0059951 | A1 | 3/2011 | Rodgers et al. |
| 2011/0207754 | A1 | 8/2011 | Li et al. |
| 2011/0224190 | A1 | 9/2011 | Huang et al. |
| 2011/0288107 | A1 | 11/2011 | Parikh et al. |
| 2012/0149681 | A1 | 6/2012 | Rodgers et al. |
| 2012/0149682 | A1 | 6/2012 | Rodgers et al. |
| 2013/0018034 | A1 | 1/2013 | Yao et al. |
| 2013/0045963 | A1 | 2/2013 | Rodgers et al. |
| 2013/0060026 | A1 | 3/2013 | Zhou et al. |
| 2014/0005166 | A1 | 1/2014 | Rodgers et al. |
| 2014/0121198 | A1 | 5/2014 | Li et al. |
| 2014/0256941 | A1 | 9/2014 | Liu et al. |
| 2014/0343030 | A1 | 11/2014 | Li et al. |
| 2015/0065447 | A1 | 3/2015 | Sandor |
| 2015/0065484 | A1 | 3/2015 | Yeleswaram et al. |
| 2015/0246046 | A1 | 9/2015 | Vaddi |
| 2015/0344497 | A1 | 12/2015 | Zhou et al. |
| 2019/0255053 | A1 | 8/2019 | Montgomery et al. |

(Continued)

FOREIGN PATENT DOCUMENTS

| | | |
|---|---|---|
| WO | WO 2002/000196 | 1/2002 |
| WO | WO 2015/131031 | 9/2015 |

(Continued)

OTHER PUBLICATIONS

Berge et al., "Pharmaceutical Salts," J Pharm Sci., 1977, 66(1):1-19.
Bose et al., "JAK2 inhibitors for myeloproliferative neoplasms: What is next?" Blood, Jul. 13, 2017, 130(2): 115-125.
Bose et al., "Management of Myelofibrosis-Related Cytopenias," Current Hematology Malignancy Reports, May 23, 2018, May 23, 2018, 13:164-172.
Danaee et al., "Selective JAK/STAT Inhibition: Signaling a Way Forward in the Management of Myelofibrosis," Journal of OncoPathology, 2014, 2(3):45-54.
El Fakih et al., "Janus Kinase Inhibitors and Stem Cell Transplantation in Myelofibrosis," Clinical Lymphoma, Myeloma and Leukemia, Jun. 1, 2015, 15:S34-S42.
Flex et al., "Somatically acquired JAK1 mutations in adult acute lymphoblastic leukemia," J Exp Med., 2008, 205:751-758.

(Continued)

*Primary Examiner* — Samantha L Shterengarts
(74) *Attorney, Agent, or Firm* — Fish & Richardson P.C.

(57) ABSTRACT

The present application relates to treatment of a hematological disease selected from leukemia, lymphoma, and multiple myeloma in a patient in need thereof, comprising administering to the patient: (a) a therapeutically effective amount of a selective JAK1 inhibitor; (b) a therapeutically effective amount of an immunomodulatory agent, and (c) a therapeutically effective amount of a steroid.

28 Claims, 5 Drawing Sheets

(56) References Cited

U.S. PATENT DOCUMENTS

| | | |
|---|---|---|
| 2019/0328739 A1 | 10/2019 | Howell et al. |
| 2019/0331697 A1 | 10/2019 | Howell et al. |
| 2020/0063188 A1 | 2/2020 | Howell et al. |
| 2020/0197399 A1 | 6/2020 | Yeleswaram et al. |
| 2020/0281931 A1 | 9/2020 | Schaub et al. |
| 2021/0107901 A1 | 4/2021 | Ye et al. |
| 2021/0123931 A1 | 4/2021 | Howell et al. |

FOREIGN PATENT DOCUMENTS

| | | |
|---|---|---|
| WO | WO 2015/184087 | 12/2015 |
| WO | WO 2015/184305 | 12/2015 |
| WO | WO 2018/067422 | 4/2018 |

OTHER PUBLICATIONS

Fonesca, et al., "Interleukin-6 as a key player in systemic inflammation and joint destruction," Autoimmunity Reviews, 2009, 8:538-542.
Gowin et al., "The New Landscape of Therapy for Myelofibrosis," Current Hematologic Malignancy Reports, Dec. 2013, 8(4):325-332.
Guschin et al., "A major role for the protein tyrosine kinase JAK1 in the JAK/STAT signal transduction pathway in response to interleukin-6," Embo J., 1995, 14:1421-1429.
Hobbs "New drugs for myelofibrosis," Expert Opinion on Orphan Drugs, May 3, 2016, 4(5):521-529.
International Search Report and Written Opinion in International Application No. PCT/US2019/059099, dated Jan. 9, 2020, 13 pages.
Iurlo et al., "Treatment of myelofibrosis: Old and new strategies," Clinical Medicine Insights: Blood Disorders, Mar. 8, 2017, 10:1-10.
Jethava "Relapse of Hodgkin lymphoma after autologous transplantation: Time to rethink treatment?" Hematology/ Oncology and Stem Cell Therapy, Jun. 2017, 10(2):47-56.
Mullighan, "JAK mutations in high-risk childhood acute lymphoblastic leukemia," Proc Natl Acad Sci USA., 2009, 106:9414-9418.
Park et al., "Homogeneous proximity tyrosine kinase assays: scintillation proximity assay versus homogeneous time-resolved fluorescence," Analytical Biochemistry, 1999, 269(1):94-104.
Remington's Pharmaceutical Sciences, $17^{th}$ Ed., Mack Publishing Company, Easton, 1985, p. 1418.
Schroeder et al., "A phase I trial of Janus kinase (JAK) inhibition with INCB039110 in acute graft-versus-host disease (aGVHD)," Blood, Meeting Info: 58th Annual Meeting of the American Society of Hematology, ASH 2016, San Diego, CA, United States, Dec. 2, 2016, 128(22):390.
Search Report ID No. 2018-094, dated Aug. 29, 2018, 38 pages.
Shreenivas et al., "Emerging drugs for the treatment of Myelofibrosis," Expert Opinion on Emerging Drugs, Jan. 2, 2018, 23(1):37-49.
Smolen et al., "Effect of interleukin-6 receptor inhibition with tocilizumab in patients with rheumatoid arthritis (OPTION study): a double-blind, placebo-controlled, randomised trial," Lancet, Mar. 22-28, 2008, 371(9617):987-997.
Sochacki et al., "Therapeutic approaches in myelofibrosis and myelodysplastic/myeloproliferative overlap syndromes," OncoTargets and Therapy, Apr. 15, 2016,9:2273-2286.
Stein et al., "Novel therapies for myelofibrosis," Leuk Lymphoma., 2015, 56(10):2768-2778.
Vainchenker et al., "JAK/STAT signaling in hematological malignancies," Oncogene, 2013, 32:2601-2613.
International Preliminary Report on Patentability in International Application No. PCT/US2019/059099, dated May 14, 2021, 7 pages.

COMBINATION THERAPY FOR TREATMENT OF HEMATOLOGICAL DISEASES

CROSS-REFERENCE TO RELATED APPLICATIONS

This application claims the benefit of U.S. Provisional Application Ser. No. 62/753,409, filed Oct. 31, 2018, the disclosure of which is incorporated herein by reference in its entirety.

TECHNICAL FIELD

The present application relates to treatment of a hematological disease selected from leukemia, lymphoma, and multiple myeloma in a patient in need thereof, comprising administering to the patient: (a) a therapeutically effective amount of a selective JAK1 inhibitor; (b) a therapeutically effective amount of an immunomodulatory agent, and (c) a therapeutically effective amount of a steroid.

BACKGROUND

The Janus kinase (JAK)/signal transducer and activator of transcription (STAT) pathway has been identified as a critical player in blood formation and immune response due to its role in signaling by cytokine receptors, a superfamily of more than 30 transmembrane proteins that recognize specific cytokines. (Vainchenker et al. *Oncogene*, 2013, 32, 2601-2613). As such, dysregulation of the JAK/STAT pathway is implicated in hematological malignancies. (Vainchenker et al. *Oncogene*, 2013, 32, 2601-2613).

Current therapies for hematological disorders, such as multiple myeloma, often fail to cure the disease and nearly all patients eventually develop resistance to these therapies. Thus, there is a need for new therapies to improve patient outcome. This application is directed to this need and others.

SUMMARY

Figure 1:
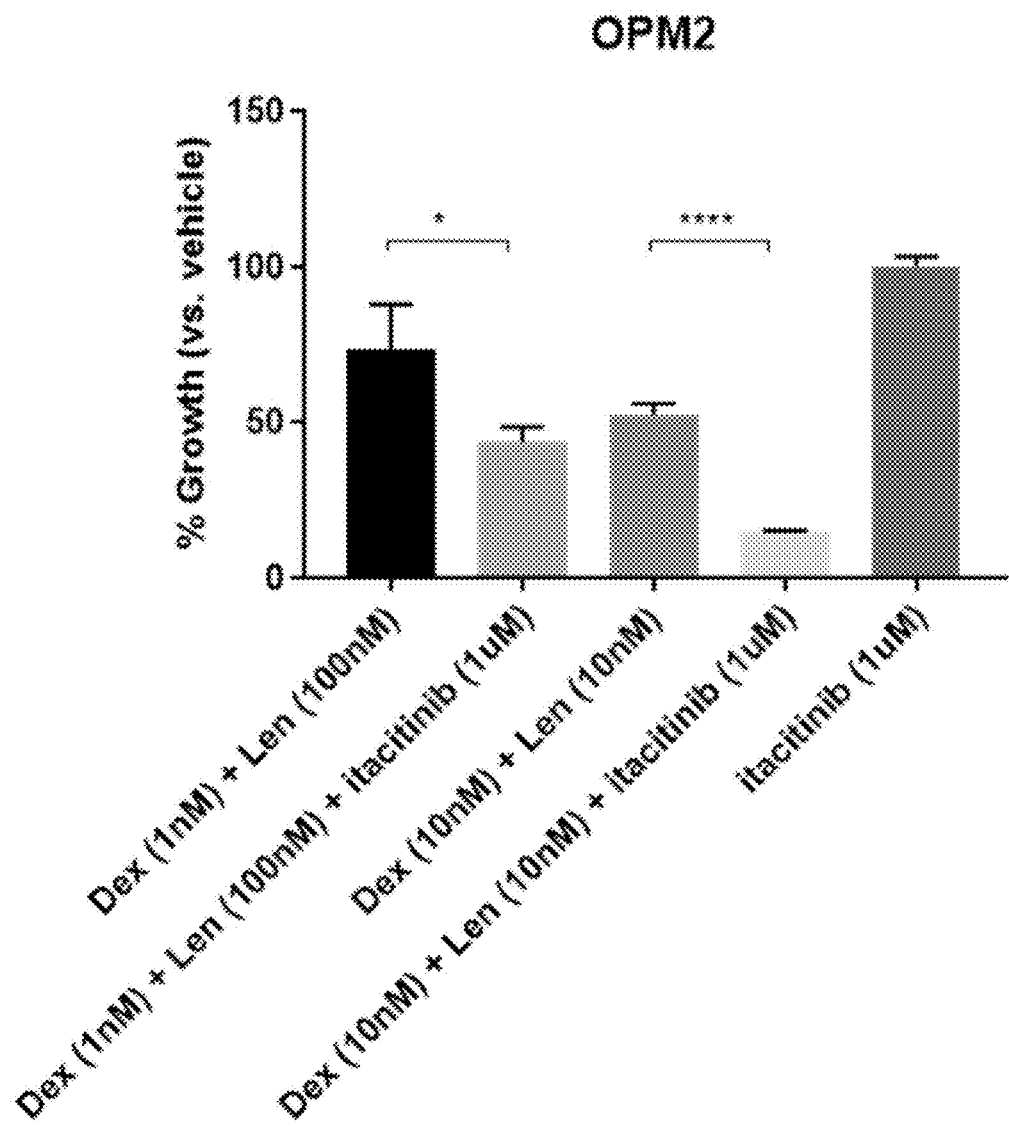
FIGS. 1-5 show results of in vitro analyses of itacitinib/lenalidomide/dexamethasone combination therapies on the viability of human multiple myeloma cell lines OPM2 (FIG. 1), KMS11 (FIG. 2), KMS12BM (FIG. 3), MM1.R (FIG. 4), and MM1.S (FIG. 5).

The present application provides, inter alia, methods of treating a hematological disease selected from leukemia, lymphoma, and multiple myeloma in a patient in need thereof, comprising administering to the patient: (a) a therapeutically effective amount of a selective JAK1 inhibitor; (b) a therapeutically effective amount of an immunomodulatory agent, and (c) a therapeutically effective amount of a steroid.

The present application further provides the use of the compounds at the doses recited herein for use in the manufacture of medicaments for treating a hematological disease selected from leukemia, lymphoma, and multiple myeloma.

The present application also provides the compounds at the doses recited herein for use in treating a hematological disease selected from leukemia, lymphoma, and multiple myeloma.

The details of one or more embodiments are set forth in the description below. Other features, objects, and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The present invention provides additional therapeutic options that are capable of overcoming drug resistance to hematological malignancies and improving the outcome for these patients. Specifically, the present invention relates to the use of a selective JAK1 inhibitor in combination with an immunomodulatory agent, and a steroid for treatment of a hematological disease.

Accordingly, provided herein are methods of treating a hematological disease selected from leukemia, lymphoma, and multiple myeloma in a patient in need thereof, comprising administering to the patient: (a) a therapeutically effective amount of a selective JAK1 inhibitor; (b) a therapeutically effective amount of an immunomodulatory agent, and (c) a therapeutically effective amount of a steroid.

In some embodiments, the hematological disease is chronic lymphocytic leukemia.

In some embodiments, the hematological disease is non-Hodgkin's lymphoma. In further embodiments, the non-Hodgkin's lymphoma is B-cell related.

In some embodiments, the hematological disease is multiple myeloma. In further embodiments, the multiple myeloma is relapsed, refractory, or relapsed and refractory multiple myeloma. In some embodiments, the multiple myeloma is refractory when the disease progresses during treatment (i.e., when the patient with the multiple myeloma is receiving treatment) and/or within eight weeks of the treatment completion (i.e., within eight weeks after the patient with the multiple myeloma received the last dose of treatment). In some embodiments, the multiple myeloma is relapsed when the disease progresses during the time period after eight weeks from treatment completion (i.e., more than eight weeks after the patient with the multiple myeloma received the last dose of treatment).

In some embodiments, the selective JAK1 inhibitor; the immunomodulatory agent, and the steroid can be administered simultaneously, sequentially, as part of a cyclic dosing schedule (cyclic administration), or any combination thereof.

In some embodiments, each of the selective JAK1 inhibitor; the immunomodulatory agent, and the steroid are administered as part of a cyclic dosing schedule, which means that during a cycle (e.g., 28 days) each of the selective JAK1 inhibitor; the immunomodulatory agent, and the steroid are administered, but there are one or more days within said period where only one or two of the selective JAK1 inhibitor; the immunomodulatory agent, and the steroid are administered. For example, in a 28 day cycle of treatment; the selective JAK1 inhibitor is administered on days 1-28, the immunomodulatory drug is administered on days 1-21; and the steroid is administered on days 1-28. In some embodiments, one or more of the compounds can be administered either every day or every other day throughout the cycle.

I. JAK1 Selective Inhibitors

The methods described herein utilize selective JAK1 inhibitors. A selective JAK1 inhibitor is a compound that inhibits JAK1 activity preferentially over other Janus kinases. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, et al., *Autoimmunity Reviews*, 8:538-42, 2009). Because IL-6 signals, at least in part, through JAK1, IL-6 can be indirectly through JAK1 inhibition, resulting in potential clinical benefit (Guschin, et al. *Embo J* 14:1421, 1995; Smolen, et al. Lancet 371:987, 2008). Moreover, in some cancers JAK1 is mutated resulting in constitutive undesirable tumor cell growth and survival (Mullighan, *Proc Natl Acad Sci USA*. 106:9414-8, 2009; Flex, *J Exp Med*. 205:751-8, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Using selective JAK1 inhibitors in combination with other drugs such as thalidomide or derivatives thereof, e.g., lenalidomide and a steroid, may provide a synergistic anti-cancer effect.

The selective JAK1 inhibitors described herein, or pharmaceutically acceptable salts thereof, preferentially inhibit JAK1 over one or more of JAK2, JAK3, and TYK2. In some embodiments, the selective JAK1 inhibitors inhibit JAK1 preferentially over JAK2 (e.g., have a JAK2/JAK1 $IC_{50}$ ratio>1). In some embodiments, the selective JAK1 inhibitors or salts are about 10-fold more selective for JAK1 over JAK2. In some embodiments, the selective JAK1 inhibitors or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the selective JAK1 inhibitor is a compound of Table 1, or a pharmaceutically acceptable salt thereof. The $IC_{50}$ values obtained by the method of Example A at 1 mM ATP are shown in Table 1.

TABLE 1

| Comp. No. | Prep. | Name | Structure | JAK1 IC$_{50}$ (nM) | JAK2/JAK1 |
|---|---|---|---|---|---|
| 1 | US 2011/0224190 (Example 1) | {1-{1-[3-Fluoro-2-(trifluoromethyl) isonicotinoyl] piperidin-4-yl}-3-[4-(7H-pyrrolo[2,3-d]pyrimidin-4-yl)-1H-pyrazol-1-yl]azetidin-3-yl}acetonitrile | 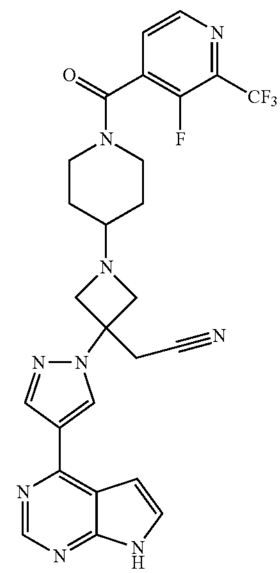 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl] piperidine-1-carboxamide | 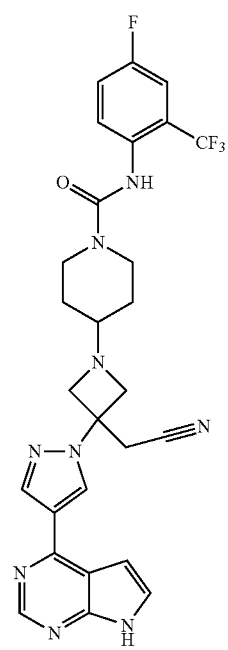 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 3 | US 2011/0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 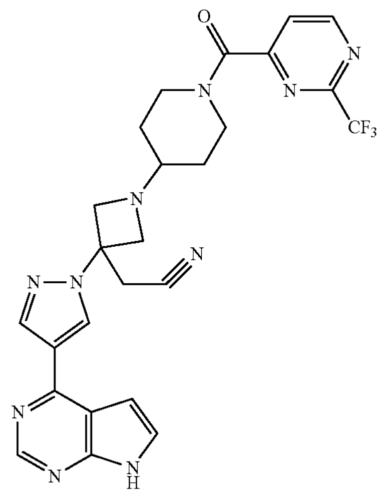 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 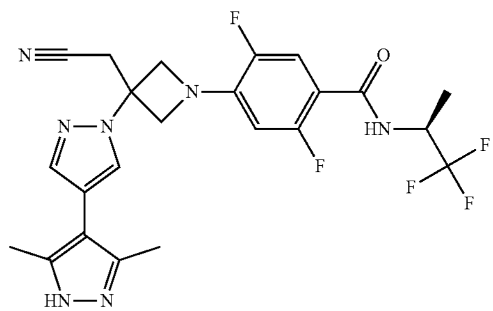 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 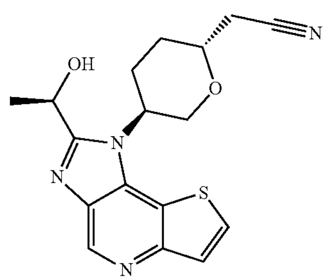 [SMILES: C[C@@H](O)c1nc2cnc3ccsc3c2n1[C@H]1CC[C@H](CC#N)OC1] | ++ | >10 |
| 6 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 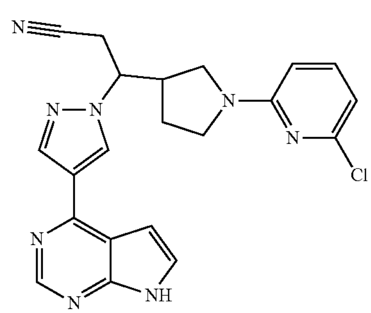 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/ JAK1 |
|---|---|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 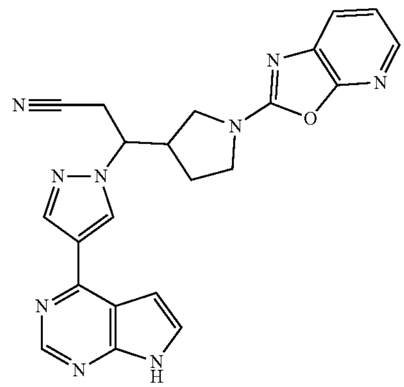 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 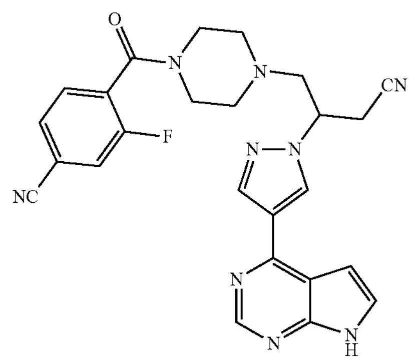 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 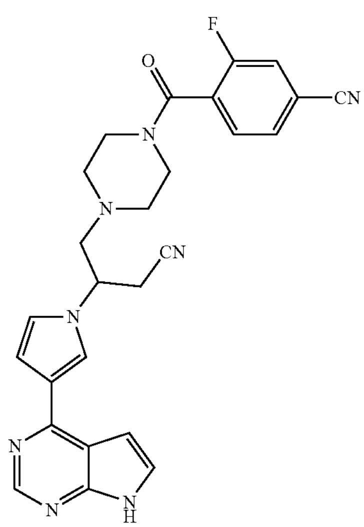 [SMILES: N#CCC(CN1CCN(C(=O)c2ccc(C#N)cc2F)CC1)n1ccc(-c2ncnc3[nH]ccc23)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 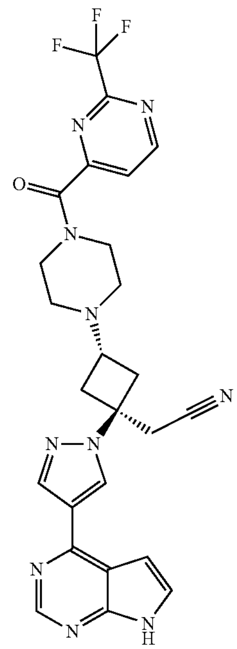 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 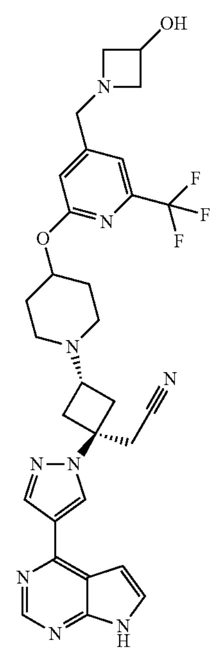 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 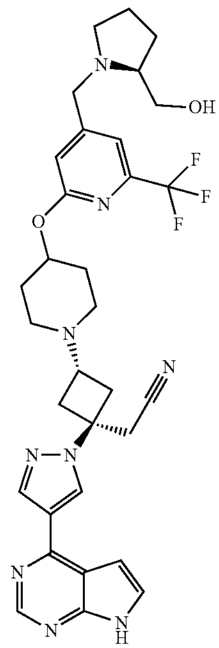 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 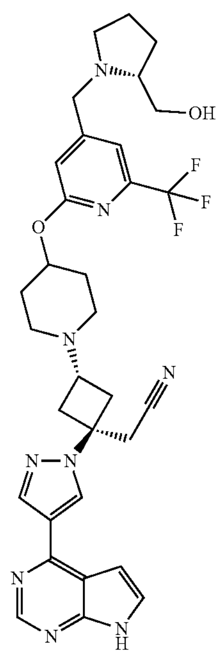 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 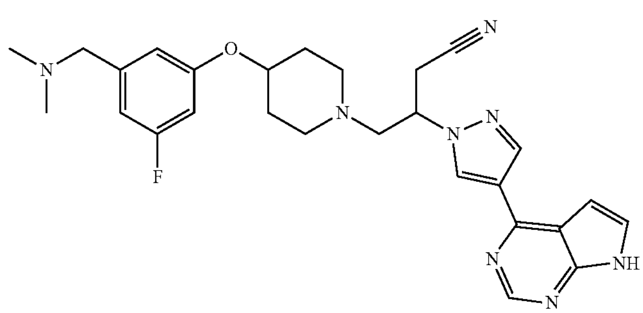 [SMILES: CN(C)Cc1cc(F)cc(OC2CCN(CC(CC#N)n3cc(-c4ncnc5[nH]ccc45)cn3)CC2)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 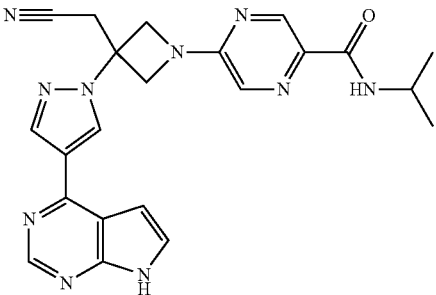 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 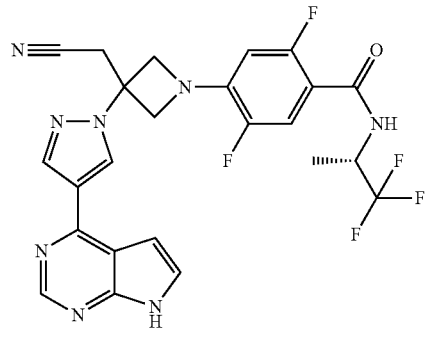 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 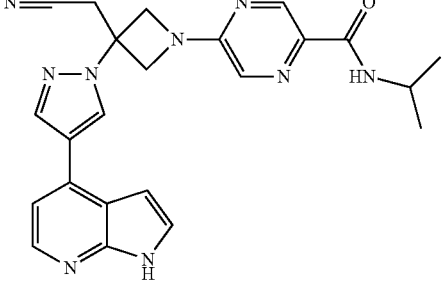 | + | >10 |
| 18 | US 2013/ 0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 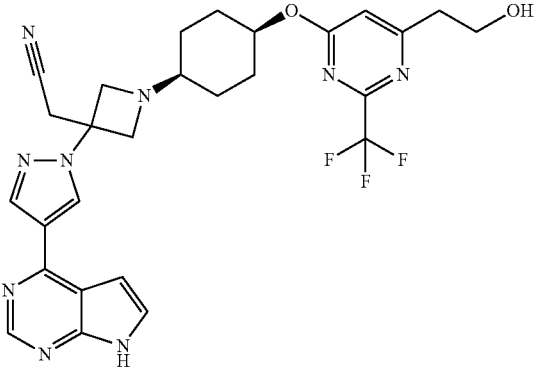 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 19 | US 2013/ 0045963 (Example 65) | {1-(cis--4{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 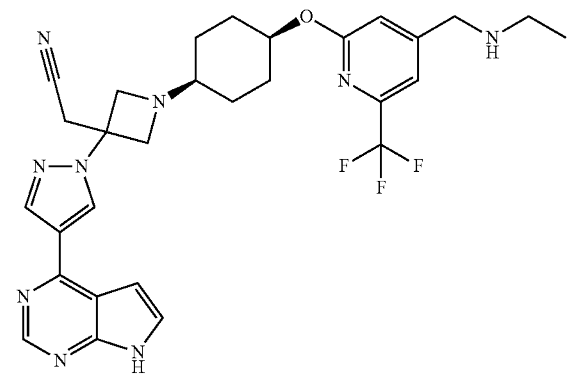 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 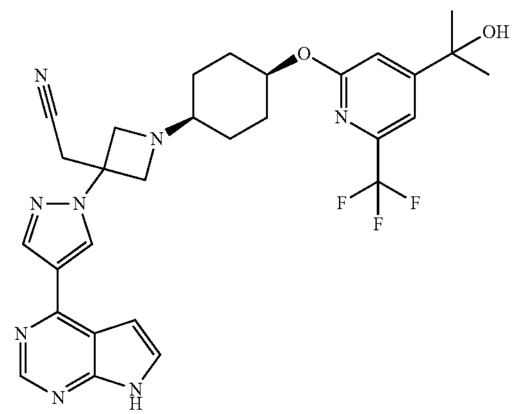 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 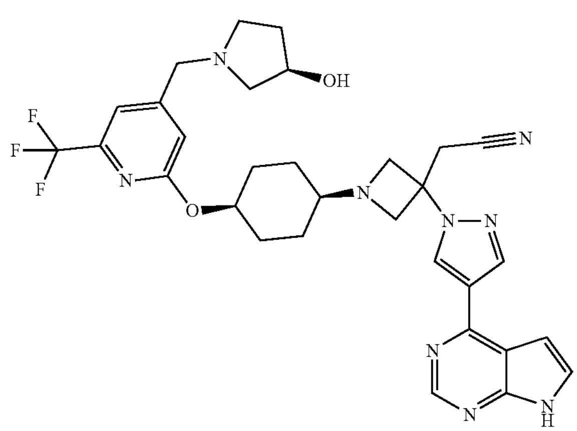 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 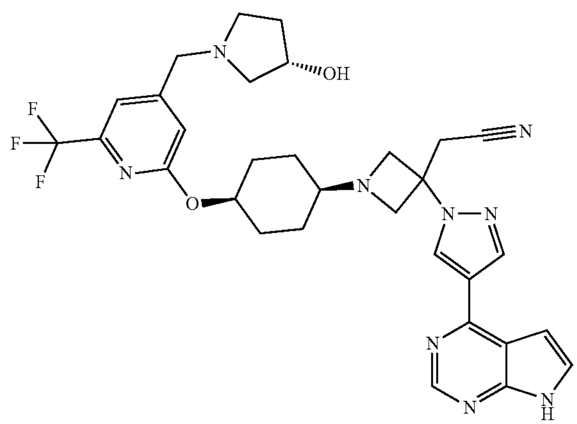 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 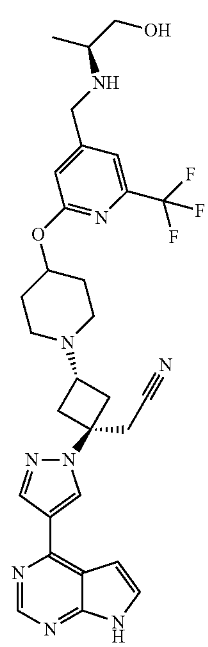 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 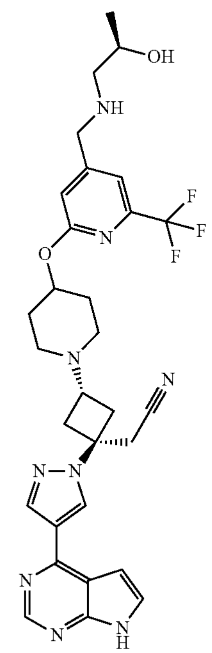 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 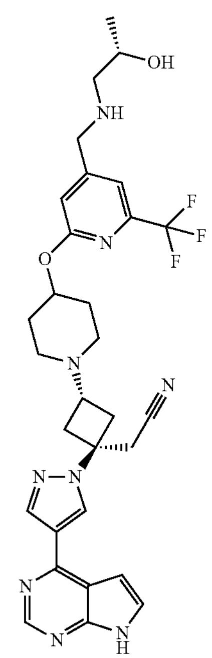 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 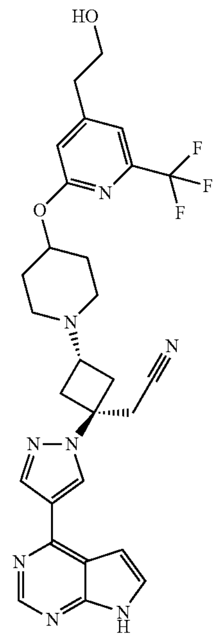 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤ 100 nM (see Example A for assay conditions)
+++ means ≤ 300 nM (see Example A for assay conditions)
$^a$Data for enantiomer 1
$^b$Data for enantiomer 2

In some embodiments, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the selective JAK1 inhibitor is 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the selective JAK1 inhibitor is 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the selective JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the selective JAK1 inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5 S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. No. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, selective JAK1 inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the selective JAK1 inhibitor is a compound of Formula I

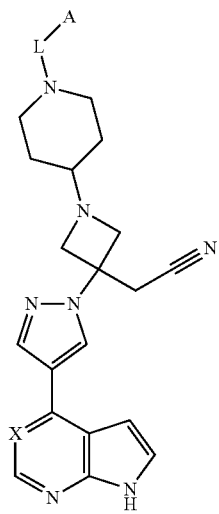

or a pharmaceutically acceptable salt thereof, wherein:

X is N or CH;

L is C(=O) or C(=O)NH;

A is phenyl, pyridinyl, or pyrimidinyl each of which is optionally substituted with 1 or 2 independently selected $R^1$ groups; and each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the selective JAK1 inhibitor is a compound of Formula II

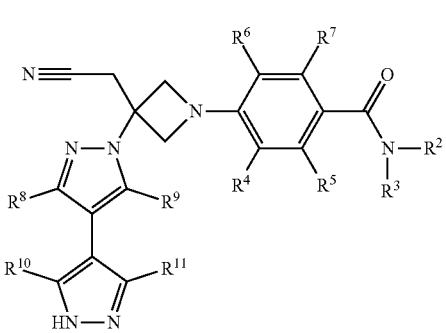

or a pharmaceutically acceptable salt thereof, wherein:

$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^3$ is H or methyl;

$R^4$ is H, F, or Cl;

$R^5$ is H or F;

$R^6$ is H or F;

$R^7$ is H or F;

$R^8$ is H or methyl;

$R^9$ is H or methyl;

$R^{10}$ is H or methyl; and $R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the selective JAK1 inhibitor is a compound of Formula III

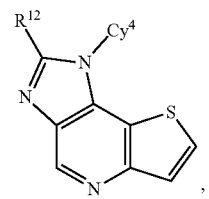

or a pharmaceutically acceptable salt thereof, wherein:

$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and $R^{12}$ is —$CH_2$—OH, —CH($CH_3$)—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the selective JAK1 inhibitor is administered in a daily amount of from about 1 mg to about 2000 mg, about 10 mg to about 2000 mg, or about 100 mg to about 2000 mg.

In some embodiments, the selective JAK1 inhibitor is administered in a daily amount of from about 100 mg to about 1200 mg on a free base basis. Accordingly, in some embodiments, the selective JAK1 inhibitor is administered in a daily amount of about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, or about 1200 mg on a free base basis.

In some embodiments, the selective JAK1 inhibitor is administered in a daily amount of from about 200 mg to about 1200 mg on a free base basis. In some embodiments, the selective JAK1 inhibitor is administered in a daily amount of from about 200 mg to about 1200 mg on a free base basis on days 1-28 in a 28 day cycle of treatment. A daily amount of from about 200 mg to about 1200 mg can be administered twice daily, e.g., by separate doses of from about 100 mg to about 600 mg.

In some embodiments, the selective JAK1 inhibitor is administered in a daily amount of from about 100 mg to about 600 mg on a free base basis.

In some embodiments, the selective JAK1 inhibitor is administered in a daily amount of from about 100 mg to about 600 mg on a free base basis on days 1-28 in a 28 day cycle of treatment.

In some embodiments the selective JAK1 inhibitor is administered once daily.

In some embodiments, the selective JAK1 inhibitor is administered twice daily.

In some embodiments, the dose of the selective JAK1 inhibitor is administered as one or more sustained-release dosage forms. Sustained-release dosage forms of the selective JAK1 inhibitor {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof (Table 1, Compound 1) can be found in US Publ. No. 2015-0065484, filed Aug. 6, 2014, which is hereby incorporated by reference in its entirety.

In some embodiments, the dose of the selective JAK1 inhibitor is administered as one or more immediate release dosage form.

II. Immunomodulatory Agents

The methods provided herein further comprise administering a therapeutically effective amount of an immunomodulatory agent.

In some embodiments, the immunomodulatory agent is selected from thalidomide, lenalidomide, apremilast, linomide, and pomalidomide, or a pharmaceutically acceptable salt thereof.

In some embodiments, the immunomodulatory agent is selected from thalidomide, lenalidomide, and pomalidomide, or a pharmaceutically acceptable salt thereof.

In some embodiments, the immunomodulatory agent is thalidomide, or a pharmaceutically acceptable salt thereof.

In some embodiments, the immunomodulatory agent is lenalidomide, or a pharmaceutically acceptable salt thereof. In further embodiments, the immunomodulatory agent is lenalidomide.

In some embodiments, the immunomodulatory agent is pomalidomide, or a pharmaceutically acceptable salt thereof.

In some embodiments, the immunomodulatory agent is apremilast, or a pharmaceutically acceptable salt thereof.

In some embodiments, the immunomodulatory agent is administered in a daily amount of from about 2.5 mg to about 25 mg on a free base basis.

In some embodiments, the immunomodulatory agent is lenalidomide, or a pharmaceutically acceptable salt thereof, and is administered in a daily amount of from about 2.5 mg to about 25 mg on a free base basis.

In some embodiments, the immunomodulatory agent is administered in a daily amount of from about 2.5 mg to about 25 mg on a free base basis on days 1-21 in a 28 day cycle of treatment.

In some embodiments, the immunomodulatory agent is administered in a daily amount of from about 5 mg to about 15 mg on a free base basis.

In some embodiments, the immunomodulatory agent is lenalidomide, or a pharmaceutically acceptable salt thereof, and is administered in a daily amount of from about 5 mg to about 15 mg on a free base basis.

In some embodiments, the immunomodulatory agent is administered in a daily amount of from about 5 mg to about 15 mg on a free base basis on days 1-21 in a 28 day cycle of treatment.

In some embodiments, the immunomodulatory agent is administered in a daily amount of about 10 mg on a free base basis.

In some embodiments, the immunomodulatory agent is lenalidomide, or a pharmaceutically acceptable salt thereof, and is administered in a daily amount of about 10 mg on a free base basis.

In some embodiments, the immunomodulatory agent is administered in a daily amount of about 10 mg on a free base basis on days 1-21 in a 28 day cycle of treatment.

III. Steroids

The methods provided herein further comprise administering a therapeutically effective amount of a steroid.

In some embodiments, the steroid is selected from the group consisting of prednisone, methylprednisolone, dexamethasone, hydroxycortisone, cortisone, desoxycorticosterone, fludrocortisone, betamethasone, prednisolone, methylprednisone, paramethasone, triamcinolone, flumethasone, fluocinolone, fluocinonide, fluprednisolone, halcinonide, flurandrenolide, meprednisone, and medrysone, or a pharmaceutically acceptable salt of any of the aforementioned.

In some embodiments, the steroid is methylprednisolone, or a pharmaceutically acceptable salt thereof.

In some embodiments, the steroid is dexamethasone, or a pharmaceutically acceptable salt thereof.

In some embodiments, the steroid is prednisone, or a pharmaceutically acceptable salt thereof.

In some embodiments, the steroid is administered in a daily amount of from about 2 mg to about 100 mg on a free base basis.

In some embodiments, the steroid is methylprednisolone, or a pharmaceutically acceptable salt thereof, and is administered in a daily amount of from about 10 mg to about 100 mg on a free base basis.

In some embodiments, the steroid is methylprednisolone, or a pharmaceutically acceptable salt thereof, and is administered in a daily amount of from about 20 mg to about 60 mg on a free base basis.

In some embodiments, the steroid is methylprednisolone, or a pharmaceutically acceptable salt thereof, and is administered in a daily amount of about 40 mg on a free base basis.

In some embodiments, the steroid is dexamethasone, or a pharmaceutically acceptable salt thereof, and is administered in a daily amount of from about 2 mg to about 20 mg on a free base basis.

In some embodiments, the steroid is administered in a daily amount of from about 20 mg to about 60 mg on a free base basis on days 1-28 in a 28 day cycle of treatment.

In some embodiments, the steroid is administered in a daily amount of from about 2 mg to about 20 mg on a free base basis on days 1-28 in a 28 day cycle of treatment.

In some embodiments, the steroid is administered in a daily amount of from about 20 mg to about 60 mg on a free base basis every other day during days 1-28 in a 28 day cycle of treatment.

In some embodiments, the steroid is administered in a daily amount of from about 2 mg to about 20 mg on a free base basis every other day during days 1-28 in a 28 day cycle of treatment.

The embodiments described herein are intended to be combined in any suitable combination as if the embodiments are multiply dependent claims (e.g., the embodiments related to the selective JAK1 inhibitor and doses of the same, the embodiments related to the immunomodulatory agent and doses of the same, the embodiment related to the steroids and doses of the same, the embodiments related to any salt forms of the compounds disclosed herein, the embodiments related to the individual types of hematological diseases, and the embodiments related to composition and/or administration can be combined in any combination).

For example, provided herein is a method of treating multiple myeloma in a patient in need thereof, comprising administering to the patient: (a) a daily amount of {1-{1-[3-fluoro-2-(trifluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, of from about 200 to about 1200 mg on a free base basis on days 1-28 in a 28 day cycle of treatment; (b) a daily amount of about 10 mg on a free base basis of lenalidomide, or a pharmaceutically acceptable salt thereof, on days 1-21 in the 28 day cycle of treatment; and (c) a daily amount of about 40 mg on a free base basis of methylprednisolone, or a pharmaceutically acceptable salt thereof, every other day during days 1-28 in the 28 day cycle of treatment.

Also provided herein is a method of treating multiple myeloma in a patient in need thereof, comprising administering to the patient: (a) a daily amount of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, of from about 200 to about 1200 mg on a free base basis on days 1-28 in a 28 day cycle of treatment; (b) a daily amount of about 10 mg on a free base basis of lenalidomide, or a pharmaceutically acceptable salt thereof, on days 1-21 in the 28 day cycle of treatment; and (c) a daily amount of about 40 mg on a free base basis of methylprednisolone, or a pharmaceutically acceptable salt thereof, on days 1-28 in the 28 day cycle of treatment.

As another example, provided herein is a method of treating multiple myeloma in a patient in need thereof, comprising administering to the patient: (a) a daily amount of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, of from about 200 to about 1200 mg on a free base basis on days 1-28 in a 28 day cycle of treatment; (b) a daily amount of lenalidomide, or a pharmaceutically acceptable salt thereof, of about 10 mg on a free base basis on days 1-21 in the 28 day cycle of treatment; and (c) a daily amount of dexamethasone, or a pharmaceutically acceptable salt thereof of from about 2 mg to about 20 mg on a free base basis on days 1-28 in the 28 day cycle of treatment.

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 1 can be optionally substituted with deuterium atoms, such as —CD$_3$ being substituted for —CH$_3$).

The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Additional Combinations

Cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the methods can further comprise the administration of one or more other kinase inhibitors. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors described herein can be combined with inhibitors of kinases associated with the PIK3/Akt/mTOR signaling pathway, such as PI3K, Akt (including Akt1, Akt2 and Akt3) and mTOR kinases.

The methods can further be used in combination with other methods of treatment, for example by chemotherapy, irradiation, or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, vorinostat, and zoledronate.

The methods can further be used in combination with one or more anti-inflammatory agents, steroids, immunosuppressants, or therapeutic anti-bodies.

When more than one pharmaceutical agent is administered to a patient, they can be administered simultaneously, sequentially, or in combination (e.g., for more than two agents).

Compositions

The compounds can be administered in the form of pharmaceutical compositions. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions can contain, as the active ingredient, the compounds, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

Kits

The present application also includes pharmaceutical kits useful, which include one or more containers containing a pharmaceutical composition comprising a therapeutically effective amount of the compound, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Example A: In Vitro JAK Kinase Assay

Selective JAK1 inhibitors that can be used in combination with an immunomodulatory agent and steroid for the treatment of hematological diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2, or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 µL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody takes place for 40 minutes and HTRF signal was measured on a Fusion plate reader (Perkin Elmer, Boston, Mass.). The compounds in Table 1 were tested in this assay and shown to have the $IC_{50}$ values in Table 1.

Example 1: Clinical Study of a JAK1 Selective Inhibitor for Treating Multiple Myeloma I. Design:
Single arm
Phase 2
Triplet: itacitinib (Compound 1, Table 1), steroid (methylprednisolone or dexamethasone), and lenalidomide
II. Primary Objective:
ORR (CR+VGPR+PR). ORR (objective response rate) is defined as the percentage of participants having a partial response (PR), very good partial response (VGPR), or complete response (CR) will be determined using the International Myeloma Working Group (IMWG) criteria after each 4-week or 28 day cycle of treatment
III. Primary Endpoint
IMWG criteria instrument
IV. Secondary Endpoints:
Overall survival (OS)
Progression free survival (PFR)
Time to Response (TTR): defined as the time from initiation of therapy to the first evidence of PR, VGPR or CR Duration of Response (DOR): measured from onset of response to the loss of response for responders Safety and Tolerability of the combination of itacitinib+lenalidomide+steroid Change and percent change in serum and urine M protein levels from baseline to each visit where the variable is measured.

Quality of Life (QOL)/symptoms instrument

V. Exploratory Endpoint

Clinical Benefit (CR+VGPR+PR+MR), wherein MR is minimal response: patients in whom some, but not all, the criteria for PR are fulfilled VI. Key Inclusion Criteria:

Relapsed/refractory multiple myeloma (RRMM) from ≥3 lines of therapy (fourth line) including an iMID and a proteasome. Patients are considered relapsed, when they progress greater than 8 weeks from their last dose of treatment. Patients are refractory when they progress while currently receiving treatment or within 8 weeks of the last dose of treatment Currently has MM with measurable disease. Specifically, the patient will exhibit a monoclonal immunoglobulin spike on serum electrophoresis of at least 0.5 g/dL and/or urine monoclonal protein levels of at least 200 mg/24 hours. For patients without measurable serum and urine M-protein levels, an involved serum free light chain assay (SFLC)>100 mgL or abnormal SFLC ratio can be used.

VII. Key Exclusion Criteria:

Corticosteroids greater than 20 mg/day prednisone or equivalent) within 3 weeks of study drug to ensure that steroid dose intensity at the beginning of the treatment is not altered by administration of steroids prior to the study.

VIII. Study Treatments:

Itacitinib (100 mg to 600 mg BID days 1-28 each cycle), lenalidomide (10 mg QD days 1-21 each cycle), steroid (e.g., methylprednisolone (MP) [40 mg QOD (every other day) or QD during days 1-28 each cycle] or dexamethasone [2 mg to 20 mg QOD or QD days 1-28 each cycle]).

Itacitinib (100 mg to 600 mg QD days 1-28 each cycle), lenalidomide (10 mg QD days 1-21 each cycle), steroid (e.g., methylprednisolone (MP) [40 mg QOD (every other day) or QD during days 1-28 each cycle] or dexamethasone [2 mg to 20 mg QOD or QD days 1-28 each cycle]).

QOD is every other day, QD is once daily, and BID is twice daily

IX. Sample Size

N=approximately 87

The hypothesis that the ORR is greater than 15% will be tested using an exact binomial distribution using a one-sided Type 1 error of ≤0.025. With 87 participants, the test has 90.7% power to reject the null hypothesis for an ORR of 30% with exact Type 1 error of 0.0167.

X. Treatment Period 6 months, 28 day cycles, with follow up for survival.

Example 2. In Vitro Analysis of Itacitinib, Lenalidomide, Dexamethasone Combination Therapy on Viability of Multiple Myeloma Cell Lines Human multiple myeloma cell lines KMS12BM, OPM2 (DSMZ), MM1.R, MM1.S (ATCC) and KMS11 (JCRB) were seeded into white 96 well plates (Greiner Bio One) at $10^4$ cells in 100 μL media. Combinations of dexamethasone (Sigma), lenalidomide (Chemscene), itacitinib, or DMSO control were then added. Doses were selected based on pilot studies designed to find sensitivities of each cell line to these agents. Each dose combination was performed in triplicate. After 72 hours, Cell Titer Glo (Promega) assays were performed as per manufacturer protocol to assess cell viability.

Figure 2:
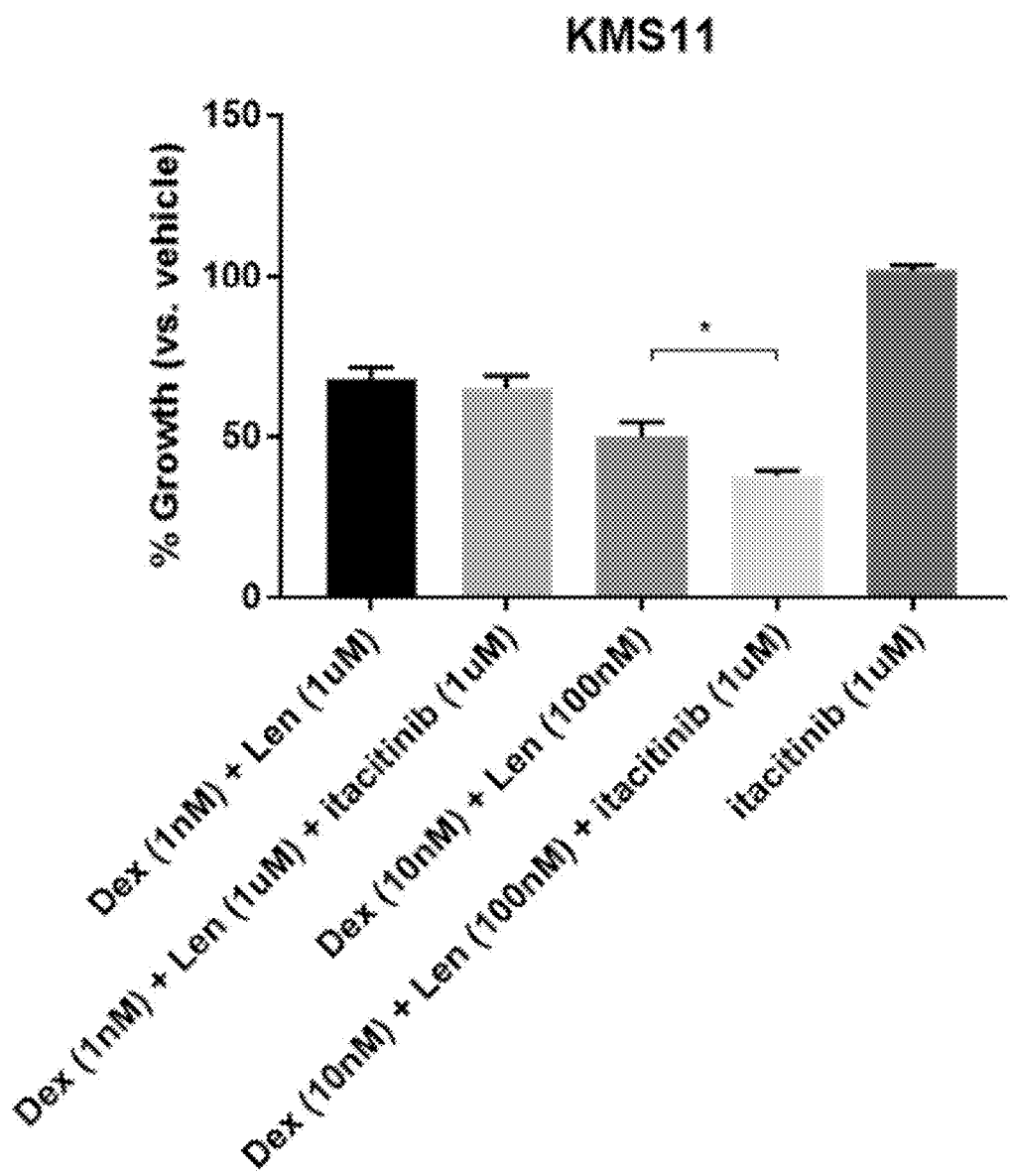
Figure 3:
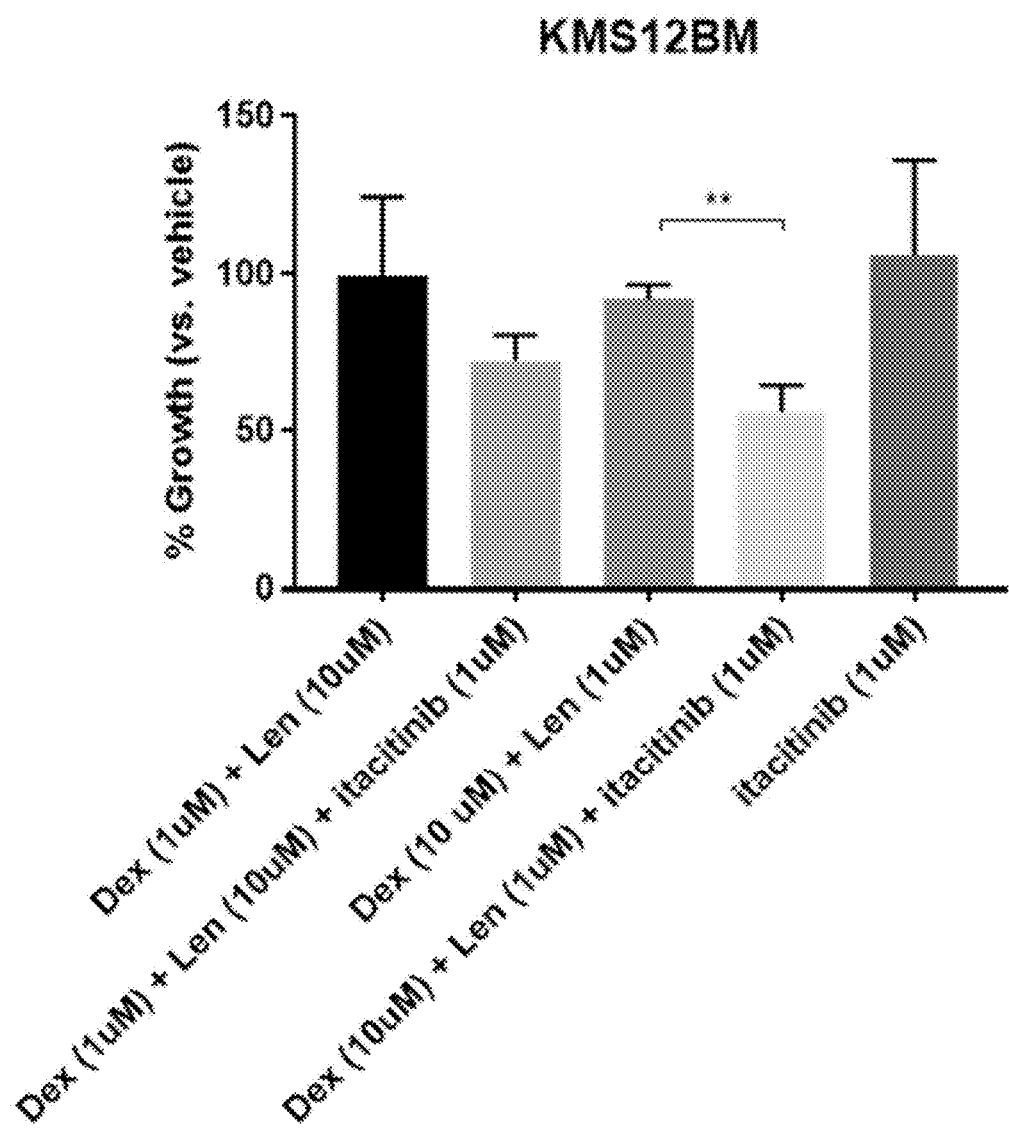
Figure 4:
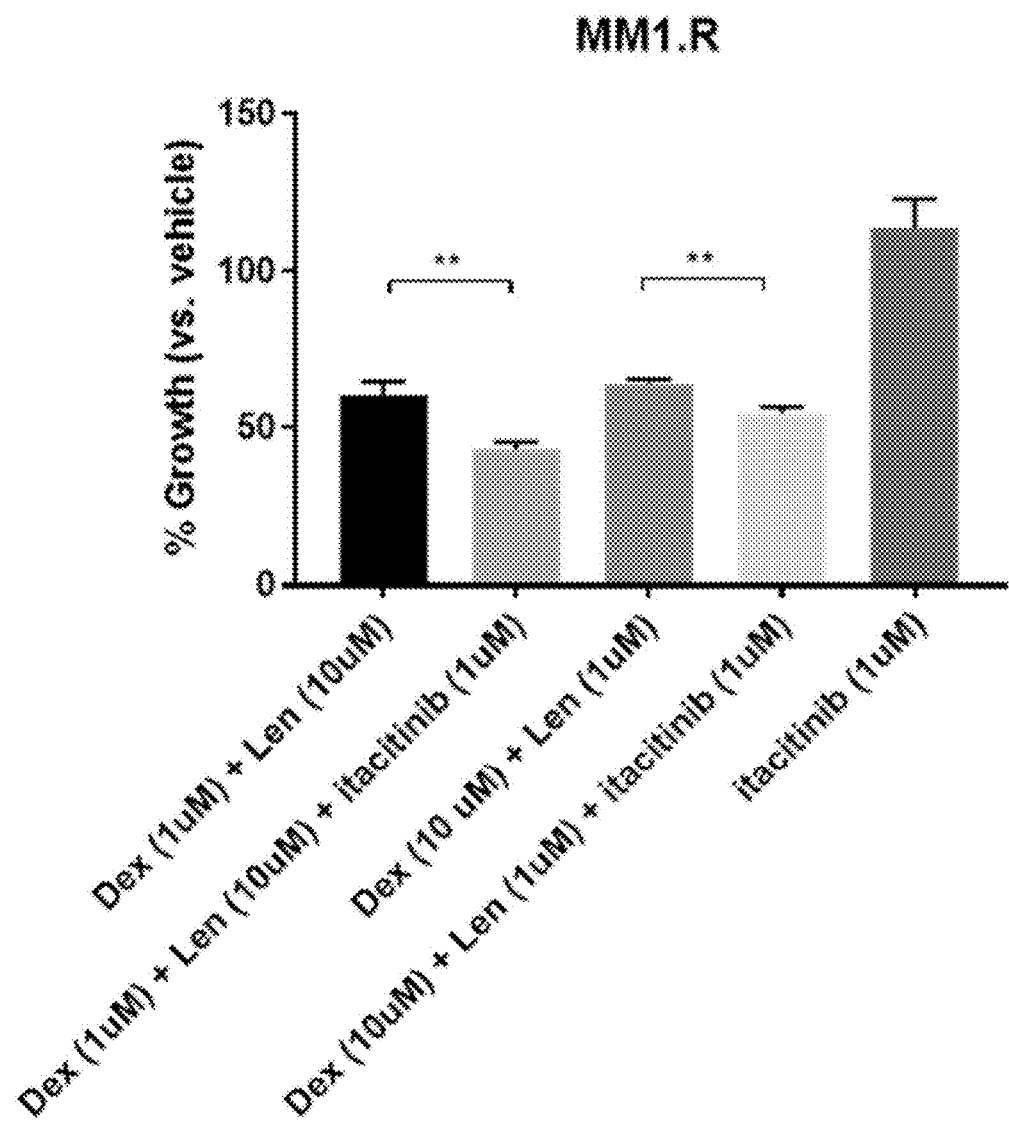
Figure 5:
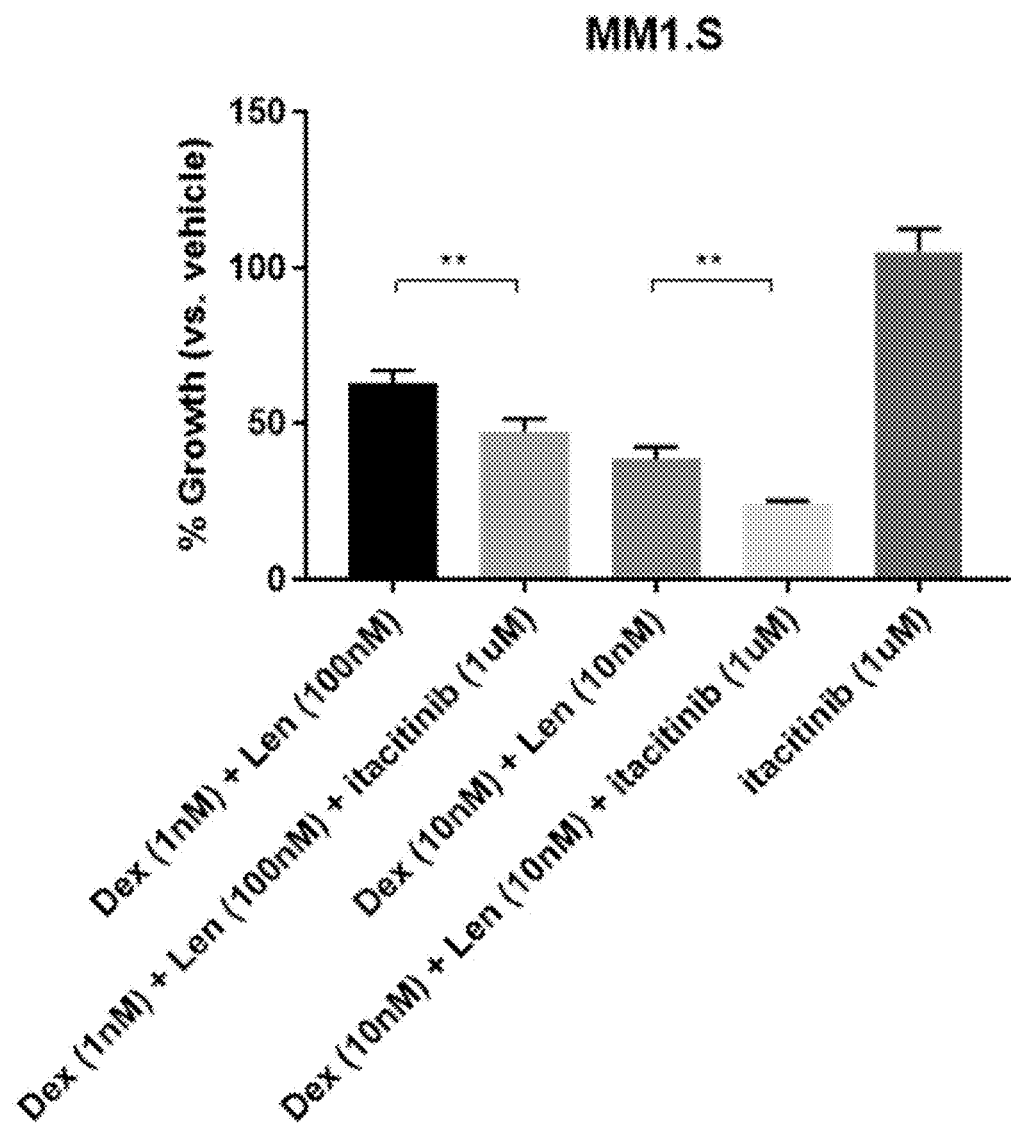

As shown in FIGS. 1-5, none of the cell lines tested were sensitive to itacitinib as a single agent, as evidence by no change in viability when compared to DMSO treated controls. Each of the cell lines were varied in their sensitivities to the lenalidomide/dexamethasone combination. Addition of itacitinib to lenalidomide/dexamethasone combination significantly decreased viability in each line tested with at least one dose of lenalidomide/dexamethasone, as shown in FIGS. 1-5.

Statistical analyses were performed using Prism Graphpad software. P values were calculated from unpaired t tests—$*p<0.05$; $p<0.01$; $**p<0.0001$). The observed decrease in viability indicated that the combination of itacitinib with lenalidomide/dexamethasone was synergistic in the tested cell lines.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of inhibiting or ameliorating a hematological disease selected from leukemia, lymphoma, and multiple myeloma in a patient in need thereof, comprising administering to the patient: (a) a therapeutically effective amount of a selective JAK1 inhibitor; (b) a therapeutically effective amount of an immunomodulatory agent, and (c) a therapeutically effective amount of a steroid; wherein:

(a) the JAK1 inhibitor is selected from:
{1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;

4-{3-(cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide;

[3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile;

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide;

((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile;

3-[1-(6-chloropyridin-2-yl)pyrrolidin-3-yl]-3-[4-(7H-pyrrolo[2,3-d]pyrimidin-4-yl)-1H-pyrazol-1-yl]propanenitrile;

3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile;

4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile;

4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile;

[trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile;

{trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile;

5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide;

4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide;

5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide;

{1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile;

{trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-({[(2R)-2-hydroxypropyl]amino)methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

{trans-3-(4-{[4-({[(2S)-2-hydroxypropyl]amino)methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile; and {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile;

or a pharmaceutically acceptable salt of any of the aforementioned;

(b) the immunomodulatory agent is selected from thalidomide, lenalidomide, apremilast, linomide, and pomalidomide, or a pharmaceutically acceptable salt of any of the aforementioned; and (c) the steroid is selected from prednisone, methylprednisolone, dexamethasone, hydroxycortisone, cortisone, desoxycorticosterone, fludrocortisone, betamethasone, prednisolone, methylprednisone, paramethasone, triamcinolone, flumethasone, fluocinolone, fluocinonide, fluprednisolone, halcinonide, flurandrenolide, meprednisone, and medrysone, or a pharmaceutically acceptable salt of any of the aforementioned.

2. The method of claim 1, wherein the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

3. The method of claim 1, wherein the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

4. The method of claim 1, wherein the immunomodulatory agent is thalidomide, or a pharmaceutically acceptable salt thereof.

5. The method of claim 1, wherein the immunomodulatory agent is lenalidomide, or a pharmaceutically acceptable salt thereof.

6. The method of claim 1, wherein the immunomodulatory agent is pomalidomide, or a pharmaceutically acceptable salt thereof.

7. The method of claim 1, wherein the immunomodulatory agent is apremilast, or a pharmaceutically acceptable salt thereof.

8. The method of claim 1, wherein the steroid is methylprednisolone, or a pharmaceutically acceptable salt thereof.

9. The method of claim 1, wherein the steroid is dexamethasone, or a pharmaceutically acceptable salt thereof.

10. The method of claim 1, wherein the steroid is prednisone, or a pharmaceutically acceptable salt thereof.

11. The method of claim 1, wherein the hematological disease is chronic lymphocytic leukemia.

12. The method of claim 1, wherein the hematological disease is non-Hodgkin's lymphoma.

13. The method of claim 12, wherein the non-Hodgkin's lymphoma is B-cell related.

14. The method of claim 1, wherein the hematological disease is multiple myeloma.

15. The method of claim 14, wherein the multiple myeloma is relapsed, refractory, or relapsed and refractory multiple myeloma.

16. The method of claim 1, wherein the hematological disease is multiple myeloma, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, the immunomodulatory agent is lenalidomide, or a pharmaceutically acceptable salt thereof; and the steroid is methylprednisolone or dexamethasone, or a pharmaceutically acceptable salt thereof.

17. The method of claim 1, wherein the hematological disease is multiple myeloma, the selective JAK1 inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, the immunomodulatory agent is lenalidomide, or a pharmaceutically acceptable salt thereof; and the steroid is dexamethasone, or a pharmaceutically acceptable salt thereof.

18. The method of claim 16, wherein the multiple myeloma is relapsed, refractory, or relapsed and refractory multiple myeloma.

19. The method of claim 1, wherein the selective JAK1 inhibitor is administered in a daily amount of from about 200 mg to about 1200 mg on a free base basis.

20. The method of claim 1, wherein the immunomodulatory agent is administered in a daily amount of from about 2.5 mg to about 25 mg on a free base basis.

21. The method of claim 1, wherein the steroid is administered in a daily amount of from about 20 mg to about 60 mg on a free base basis.

22. The method of claim 1, wherein the method comprises cyclic administration of the selective JAK1 inhibitor, the immunomodulatory agent, and the steroid, or a pharmaceutically acceptable salt thereof.

23. The method of claim 1, wherein the selective JAK1 inhibitor is administered in a daily amount of from about 200 mg to about 1200 mg on a free base basis on days 1-28 in a 28 day cycle.

24. The method of claim 1, wherein the selective JAK1 inhibitor is administered as one or more sustained-release dosage forms.

25. The method of claim 1, wherein the immunomodulatory agent is administered in a daily amount of from about 2.5 mg to about 25 mg on a free base basis on days 1-21 in a 28 day cycle.

26. The method of claim 1, wherein the steroid is administered in an amount of from about 20 mg to about 60 mg on a free base basis every other day during days 1-28 in a 28 day cycle.

27. A method of inhibiting or ameliorating multiple myeloma in a patient in need thereof, comprising administering to the patient: (a) a daily amount of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, of from about 200 to about 1200 mg on a free base basis on days 1-28 in a 28 day cycle; (b) a daily amount of lenalidomide, or a pharmaceutically acceptable salt thereof, of about 10 mg on a free base basis of on days 1-21 in the 28 day cycle; and (c) a daily amount of methylprednisolone, or a pharmaceutically acceptable salt thereof, of about 40 mg on a free base basis every other day during days 1-28 in the 28 day cycle.

28. A method of inhibiting or ameliorating multiple myeloma in a patient in need thereof, comprising administering to the patient: (a) a daily amount of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof, of from about 200 to about 1200 mg on a free base basis on days 1-28 in a 28 day cycle; (b) a daily amount of lenalidomide, or a pharmaceutically acceptable salt thereof, of about 10 mg on a free base basis on days 1-21 in the 28 day cycle; and (c) a daily amount of dexamethasone, or a pharmaceutically acceptable salt thereof, of from about 2 mg to about 20 mg on a free base basis on days 1-28 in the 28 day cycle.

* * * * *